(12) United States Patent
McKay et al.

(10) Patent No.: US 8,057,458 B2
(45) Date of Patent: Nov. 15, 2011

(54) METHOD FOR TREATING FACET PAIN

(75) Inventors: William F. McKay, Memphis, TN (US); Susan J. Drapeau, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 800 days.

(21) Appl. No.: 11/589,410

(22) Filed: Oct. 30, 2006

(65) Prior Publication Data
US 2008/0177218 A1 Jul. 24, 2008

(51) Int. Cl.
- *A61M 31/00* (2006.01)
- *A61N 1/30* (2006.01)
- *A61F 2/44* (2006.01)
- *A61F 2/00* (2006.01)
- *A61B 17/88* (2006.01)

(52) U.S. Cl. .......... 604/500; 604/506; 604/522; 604/19; 623/17.16; 606/279; 424/423

(58) Field of Classification Search ................. 604/506, 604/19, 500; 514/12; 623/17.11, 17.16; 424/145.1, 426
See application file for complete search history.

(56) References Cited

U.S. PATENT DOCUMENTS

| | | | |
|---|---|---|---|
| 3,026,248 A | 3/1962 | Noseworthy et al. | |
| 4,020,162 A | 4/1977 | Ghilardi et al. | |
| 4,451,447 A | 5/1984 | Kaplan et al. | |
| 5,605,687 A | 2/1997 | Lee et al. | |
| 5,769,899 A | 6/1998 | Schwartz et al. | |
| 6,648,916 B1 | 11/2003 | McKay | |
| 6,648,918 B2 | 11/2003 | Ferree | |
| 6,991,654 B2 | 1/2006 | Foley | |
| 2002/0016583 A1* | 2/2002 | Cragg | 604/500 |
| 2004/0054414 A1 | 3/2004 | Trieu et al. | |
| 2004/0059418 A1 | 3/2004 | McKay et al. | |
| 2004/0228901 A1 | 11/2004 | Trieu et al. | |
| 2005/0025765 A1* | 2/2005 | DiMauro et al. | 424/145.1 |
| 2005/0075288 A1* | 4/2005 | Maglione et al. | 514/12 |
| 2005/0119754 A1* | 6/2005 | Trieu et al. | 623/17.16 |
| 2005/0187631 A1 | 8/2005 | Van Hoeck et al. | |
| 2005/0197707 A1 | 9/2005 | Trieu et al. | |
| 2006/0041311 A1* | 2/2006 | McLeer | 623/17.11 |
| 2006/0046961 A1* | 3/2006 | McKay et al. | 514/12 |
| 2006/0106364 A1* | 5/2006 | Whitlock et al. | 604/506 |
| 2006/0194726 A1* | 8/2006 | Rueger et al. | 514/12 |
| 2007/0122817 A1* | 5/2007 | Church et al. | 435/6 |

FOREIGN PATENT DOCUMENTS

| | | |
|---|---|---|
| GB | 1250304 A | 10/1971 |
| GB | 1286351 A | 8/1972 |
| WO | WO01/28544 A | 4/2001 |

OTHER PUBLICATIONS

Kaptanoglu et al., "Effects of magnesium sulphate in experimental spinal cord injury: evaluation with ultrastructural findings and early clinical results," Journal of Clinical Neuroscience (2003); vol. 10, No. 3, pp. 329-334.
Borgens R B and Bohnert D., "Rapid recovery from spinal cord injury after subcutaneously administered polyetheylene glycol," Journal of Neuroscience Research (2001); vol. 66, pp. 1179-1186.
Ditor D S et al., "Effects of polyethylene glycol and magnesium sulfate administration on cinically relevant neurological outcomes after spinal cord injury in the rat," Journal of Neuroscience Research (2007); vol. 85, pp. 1458-1467.
The International Search Report and The Written Opinion of the International Searching Authority in PCT/US2007/067580.
Gregory A. Helm, et al., Gene-based therapies for the induction of spinal fusion, Neurosurg Focus, 10(4), Article 5, 2001, 1-5.
Sally R. Frenkel et al., Degradation and Repair of Articular Cartilage, Frontiers in Bioscience, 4, 671-685, Oct. 15, 1999.

\* cited by examiner

*Primary Examiner* — Theodore Stigell
*Assistant Examiner* — Bradley Thomas, Jr.

(57) ABSTRACT

A method for treating a facet pain in a subject by providing an effective amount of therapeutic agent in manner that by a biological repair effect on the facet is produced as compared to a temporary anti-inflammatory effect.

12 Claims, No Drawings

METHOD FOR TREATING FACET PAIN

BACKGROUND OF THE INVENTION

Lower back pain is the most common musculoskeletal disorder of industrialized society and the most common cause of disability in persons younger than 45 years. Given that 90% of adults experience lower back pain sometime in their life, this is the most costly of all medical diagnoses when time off from work, long-term disability, and medical and legal expenses are taken into account.

The lumbosacral facet joint is believed to be the source of pain in 15-40% of patients with chronic lower back pain and it is well known that facet pain is the etiology for most cases of mechanical lower back pain. The facet joints (posterior zygo-apophyseal joints) are diarthrodial joints with a synovial lining, the surfaces of which are covered with hyaline cartilage, which is susceptible to arthritic changes and arthropathies. Like any synovial joint, degeneration, inflammation, and injury can lead to pain with joint motion, causing restriction of motion secondary to pain, and thus deconditioning.

The articular cartilaginous surfaces found within the facet joint can degenerate due to mechanical or biological factors and cause pain as with other joint osteoarthritis. For example, a patient may suffer from arthritic facet joints, severe facet joint tropism or otherwise deformed facet joints, facet joint injuries, etc. There is currently a lack of suitable intervention procedures for facet joint disorders. Facet blocks with anesthetic and cortisone, facet denervation procedures, radiofrequency ablation of the nerve supply to the joint, or even spinal fusions have been recommended. In the early stages of degeneration, pain may be controlled by blocking the medial branch of the lumbar facet joints providing temporary relief of pain.

Percutaneous radiofrequency neurotomy is a method of denaturing the nerves that innervate the facet joint through coagulation, thus conferring temporary relief of pain. Once the axons regenerate, pain often returns. The therapeutic benefit of this procedure remains controversial.

Facetectomy, or the removal of the facet joints, may provide some relief, but significantly decreases the stiffness of the spinal column (i.e., hypermobility) in all planes of motion: flexion and extension, lateral bending, and rotation. Furthermore, problems with the facet joints can also complicate treatments associated with other portions of the spine.

Intra-articular facet joint injection with corticosteroids and a local anesthetic is one of the interventional procedures performed. The long-term benefit of intra-articular injection remains controversial. Accordingly, there is a need for a facet joint treatment that addresses these concerns.

U.S. Pat. No. 6,648,918 to McKay et.al., discloses fusion implants for promoting bone growth in intervertebral disc space. Collagen soaked Bone Morphogenic Proteins (BMP's) is disclosed as a carrier in the implanted device.

U.S. Pat. No. 5,769,899 to Schwartz et.al., discloses a bio-absorbable cartilage repair system for regenerating damaged or destroyed cartilage using hyaluronic acid.

US Patent Application 2005-00025765 to DiMauro et.al., discloses administration of therapeutic inhibitors specific to the pro-inflammatory molecules to inflamed joints. Preferably growth factors such as BMP's were delivered after the inhibition of the pro-inflammatory molecules had taken effect. Accordingly, Dimauro does not teach a procedure involving directly administering a therapeutic agent to obtain a biological repair effect.

US Patent Application 2004-0228901 to Frieu et.al., discloses injection of collagen to a synovial joint including a facet joint. US Patent Application 2004-059418 to McKay et.al., discloses treating degenerating synovial joints and facet joints.

Given the above, it is desirable to have a lasting treatment for facet pain rather than providing temporary relief.

SUMMARY OF THE INVENTION

The present invention addresses this and other problems associated with the prior art by providing a method for treating a facet pain in a subject comprising providing an effective amount of therapeutic agent whereby a biological repair effect on the facet joint is produced as compared to a temporary anti-inflammatory effect.

While not being bound by any theory, applicants believe that the biological repair effect provides for long term therapeutic value of treatment of facet joints. Rather than temporary treatment, the present invention provides for repair and regeneration of the facet cartilage, facet joint, or subchondral bone.

In an embodiment of the invention, a therapeutic agent is injected into a facet joint. In another embodiment the therapeutic agent is delivered as an injection into the subchondral bone. In another embodiment, the therapeutic agent is delivered by injection near the facet joint. In yet another embodiment the therapeutic agent is delivered through a patch or gel application to the exterior of the facet joint, or via a protruding implant into the facet joint.

In another aspect there is provided a method for repairing the articular cartilage surface of a facet joint comprising providing an effective amount of therapeutic agent whereby a biological repair effect on the facet is produced as compared to a temporary anti-inflammatory effect.

In yet another aspect there is provided a method for treating a facet pain in a subject comprising providing an effective amount of therapeutic agent and an dehydrated hydrogel creating a lasting or a temporary spacer within the facet joint whereby a biological repair effect on the facet joint is produced as compared to a temporary anti-inflammatory effect.

DETAILED DESCRIPTION OF THE INVENTION

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

Definitions

To aid in the understanding of the invention, the following non-limiting definitions are provided:

The term "subject" shall mean any animal belonging to phylum Chordata, including, without limitation, humans.

The term "treating" or "treatment" of a disease refers to executing a protocol, which may include administering one or more drugs to a subject (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the subject.

The term "therapeutic agent" is any agent that promotes the biological repair of the facet joint. The facet joint can be an acutely injured facet joint. The therapeutic agent can include a cell, a hydrogel, a growth factor, as well as mixtures thereof.

A "lubricant" is a substance that lubricates the facet joint.

A "hydrogel" is an organic polymer (natural or synthetic) is set or solidified to create a three-dimensional open-lattice structure that entraps molecules of water or other solution to form a gel.

The "biological repair effect" is any effect that halts or reverses facet joint degeneration by actively participating in repair of facet structures. The term biological repair effect may include any effect that promotes the growth or regeneration of bone tissue, the facet joint, or cartilage within a facet joint. Biological repair effects include articular cartilage surface defect, small ligamentous facet joint tears and/or subchondral bone defects.

Facet Joint

The facet joint also known as the zygapophyseal joint, bridges the vertebrae behind the vertebral foramina. It was determined that the etiology of facet joint degeneration was secondary to intervertebral disk degeneration. See G Malanga, *Lubofacral Facet Syndrome*, e-medicine, HTML document, Jul. 22, 2004.

Inflammation

The facet joints contain nociceptive nerve fibers, which can be activated by local pressure and capsular stretch, and likely provide proprioceptive and protective information to the central nervous system. In addition, the facet joints have been found to undergo sensitization of neurons by naturally occurring inflammatory mediators such as substance P and phospholipase A2. Peripheral nerve endings release chemical mediators such as bradykinin, serotonin, histamine, and prostaglandins, which are noxious and can cause pain. Substance P has been implicated because of its ability to act directly on nerve endings or indirectly through vasodilation, plasma extravasation, and histamine release. Phospholipase A2 hydrolyzes phospholipids to produce arachidonic acid, causing an inflammatory reaction, edema, and prolonged nociceptive excitation.

Disc Degeneration

The facet joints are part of an interdependent functional spinal unit consisting of the disc-vertebral body joint and the 2 facet joints, with the facets paired along the entire posterolateral vertebral column. The facet joint is considered a motion-restricting joint, able to resist stress and withstand both axial and shearing forces. In back extension, the facet joints, along with the intervertebral discs, absorb a compressive load. The overloaded facet joint then causes posterior rotation of the inferior facet, resulting in stretching of the facet joint capsule.

If one considers the disc and facet joints as an interdependent functional spinal unit, degenerative changes within this 3-joint complex can influence each of the segments. Thus, degeneration of the discs can lead to loss of disc height, resulting in a relative increase in facet load found in compression and extension maneuvers. One theory is that these excessive facet loads cause the inferior facet to pivot about the pars and stretch the joint capsule, in addition to causing rostrocaudal subluxation (ie, facet malalignment). Thus, some authors postulate that facet joints undergo osteoarthritic changes in response to disc degeneration secondary to changes in loading.

In all, many sources of pain can be found at the facet joint, ranging from degenerative changes to irritated nerve endings (chemical and mechanical) to concomitant nerve root entrapment.

In osteoarthritis, often high levels of the cytokines present in the hyaline cartilage mediate degradation of the extracellular matrix of the cartilage. Further, enzymes in the synovial fluid upregulate both matrix metalloproteinases (MMP's) and downregulate MMP inhibitors. The MMP's (under mediation by the cytokines) begin cleaving the water-retaining portions of the proteoglycans, thereby reducing its water-retaining and lubricious qualities. This degradation leads to a less lubricious hyaline cartilage, thereby increasing the wear upon the hyaline cartilage. This degenerative cascade also often leads to inflammation of the synovial lining, which often produces a thickening and fibrillation of the synovium, and the creation of finger-like villae with the synovium. When the natural regeneration of these cartilage layers is slower than this degenerative process, these changes cause even more mechanical instability, thereby causing the hyaline cartilage cells, the synovium cells and the invading macrophages to emit even more cytokines, thereby typically upregulating MMP's.

Therapeutic Agents

As used herein, the term "therapeutic agents" comprises growth factors that modulate the growth or differentiation of other cells, particularly connective tissue progenitor cells. Therapeutic agents are administered concurrently with any anti-inflammatory agent or lubricating agent prior to or after its effect has been realized. The therapeutic agents that may be used in accordance with the present invention include, but are not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs; the TGF-β superfamily, including TGF-β1, 2 and 3; osteoid-inducing factor (OIF); angiogenin(s); endothelins; hepatocyte growth factor and keratinocyte growth factor; members of the bone morphogenetic proteins (BMP's) BMP-1, BMP-3, BMP-2; OP-1, BMP-2A, BMP-2B, and BMP-7; HBGF-1 and HBGF-2; growth differentiation factors (GDF's); members of the hedgehog family of proteins, including indian, sonic and desert hedgehog; ADMP-1; other members of the interleukin (IL) family; and members of the colony-stimulating factor (CSF) family, including CSF-1, G-CSF, and GM-CSF, and isoforms thereof; and VEGF.

In some embodiments, the therapeutic agent is selected from the group consisting of TGF-B, bFGF, and IGF-1. These therapeutic agents are believed to promote regeneration of the hyaline articular cartilage. In some embodiments, the therapeutic agent is TGF-B. More preferably, TGF-B is administered in an amount of between 0.01 ng/ml and 10 mg/ml, more preferably between 0.05 ng/ml and 1 μg/ml. See DeFail et.al., *Controlled release of bioactive TGF-beta 1 from microspheres embedded within biodegradable hydrogels. Biomaterials*, 2006 March; 27(8):1579-85. Epub 2005 Sep. 6.

Suitable therapeutic agents of the Bone Morphogenic Proteins family have been used in gene therapy for induction of spinal fusion in animals. See *Gene-based therapies for the induction of spinal fusion*, Helm, et.al., Neurosurg Focus, 10(4), Article 5, 2001, 1-5. BMP-2 has shown beneficial effects of knee articular cartilage repair in animals and therefore is preferred for facet repair. LMP (LIM mineralization protein) and other soft tissue cytokines have been shown to upregulate BMP production and may be an effective treatment. LMP can be delivered as a peptide sequence in nanogram to microgram quantities, or can be administered via gene therapy in the range of 1 to 10e6 MOI.

The therapeutic agent can comprise cells. Suitable cells include, without limitation, mesenchymal stem cells, periosteal cells, pluripotent stem cells, embryonic stem cells, osteoprogentior cells, osteoblasts, osteoclasts, bone marrow-derived cell lines, and any combination thereof.

The therapeutic agent can also comprise chrondotion sulfate and/or glucosamine. These natural substances are available as nutraceuticals, and have been used by osteoarthritis patients to relieve joint pain for decades. Clinical trials, many in Europe, have demonstrated the benefit of these substances by oral administration. By delivery directly to the facet joint space, as described herein, these reagents can be given at lower doses and can directly treat the facet joint in pain. As an adjunct to the therapeutic agent described here, these materials may be useful in rebuilding and maintaining the facet joint surface.

Hyaluronic Acid

The therapeutic agent comprises glycosaminoglycans (GAGS) consisting of Hyaluronic acid. Hyaluronic acid is a high molecular weight polysaccharide of N-acetyl glucosamine and glucuronic acid molecules that is naturally occurring in all mammals in a variety of tissue and some bacterial species. In general, GAGS are biopolymers consisting of repeating polysaccharide units, and are present in nature on the cell surface as well as in the extracellular matrix of animals. GAGS are long unbranched polysaccharides containing a repeating disaccharide unit. GAGS in addition to increasing viscosity possess low compressability, which makes these molecules ideal for a lubricating fluid in the facet joints. Their rigidity provides structural integrity to cells and provides passageways between cells, allowing for cell migration.

For the purposes of this invention, hyaluronic acid includes any derivatives such as hyaluronan and hyaluronic acid itself with $H^+$ ion attached to the $COO^-$ group, and salts of hyaluronic acid whereby another positive ion replaces the $H^+$ ion, as for example, with $Na^+$ which forms sodium hyaluronate. Also included in the definition of hyaluronic acid is any physically or chemically cross-linked hyaluronic acid or derivative. Hyaluronic acid polymers are very large with molecular weights of between about 100,000 and 10,000,000 and can displace a large volume of water.

Preferably, the therapeutic agent is selected from the group consisting of hyaluronic acid and hyaluronate (either cross-linked or uncross-linked). Delivery of hyaluronic acid of varying concentrations and molecular weights have demonstrated pain relief in osteoarthritis patients. These materials can be derived from various animal sources, or can be produced through culture or synthetic assembly methods.

For the purposes of the present invention, a preferred embodiment includes a non-cross linked hyaluronic acid with a molecular weight of 0.5-10 M Dalton.

Sustained Release

In another embodiment of the present invention, the therapeutic agent may be presented in a sustained-release formulation.

Suitable sustained-release formulations include but not limited to capsules, microspheres, particles, gels, coating, matrices, wafers, pills or other pharmaceutical delivery compositions. The examples of such sustained-release formulations have been described previously, for example, in U.S. Pat. Nos. 6,953,593, 6,946,146, 6,656,508, 6,541,033, 6,451,346, the contents of which are incorporated herein by reference. Many methods of preparation of a sustained-release formulation are known in the art and are disclosed in *Remington's Pharmaceutical Sciences* (18th ed.; Mack Publishing Company, Eaton, Pa., 1990), incorporated herein by reference.

The device can include a plurality of macrospheres having outer shells of varying thickness, so that the sequential breakdown of the outer shells provides periodic release of the therapeutic agent.

Generally, the therapeutic agent can be entrapped in semipermeable matrices of solid hydrophobic polymers. The matrices can be shaped into films or microcapsules. Examples of such matrices include, but are not limited to, polyesters, copolymers of L-glutamic acid and gamma ethyl-L-glutamate (Sidman et al. (1983) *Biopolymers* 22:547-556), polylactides (U.S. Pat. No. 3,773,919 and EP 58,481), polylactate polyglycolate (PLGA) such as polylactide-co-glycolide (see, for example, U.S. Pat. Nos. 4,767,628 and 5,654,008), hydrogels (see, for example, Langer et al. (1981) *J. Biomed. Mater. Res.* 15:167-277; Langer (1982) *Chem. Tech.* 12:98-105), non-degradable ethylene-vinyl acetate (e.g. ethylene vinyl acetate disks and poly(ethylene-co-vinyl acetate)), degradable lactic acid-glycolic acid copolymers such as the Lupron Depot™, poly-D-(−)-3-hydroxybutyric acid (EP 133,988), hyaluronic acid gels (see, for example, U.S. Pat. No. 4,636,524), alginic acid suspensions, polyorthoesters (POE), and the like.

Suitable microcapsules can also include hydroxymethylcellulose or gelatin-microcapsules and polymethyl methacrylate microcapsules prepared by coacervation techniques or by interfacial polymerization. See the PCT publication WO 99/24061 entitled "Method for Producing Sustained-release Formulations," wherein a protein is encapsulated in PLGA microspheres, herein incorporated by reference. In addition, microemulsions or colloidal drug delivery systems such as liposomes and albumin microspheres, may also be used. See *Remington's Pharmaceutical Sciences* (18$^{th}$ ed.; Mack Publishing Company Co., Eaton, Pa., 1990). Other preferred sustained-release compositions employ a bioadhesive to retain therapeutic agent at the site of administration.

The sustained-release formulation may comprise a biodegradable polymer, which may provide for non-immediate release. Non-limiting examples of biodegradable polymers suitable for the sustained-release formulations include poly (alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyorthoesters (POE), or any combinations thereof, as described, for example, in the U.S. Pat. Nos. 6,991,654 and 20050187631, each of which is incorporated herein by reference in its entirety.

A person of ordinary skill will appreciate that different combinations of the sustained-release formulations are also suitable for this invention. For example, the practitioner may formulate the non-steroidal anti-inflammatory compound as a combination of a gel and microspheres loaded with the at least one anti-inflammatory compound, wherein the combination of gel and microspheres are placed in the bone defect.

In the practice of the invention, the administration is localized and sustained. For example, depending on the carrier, the sustained-release formulations, and the total amount of the therapeutic agent, the practitioner can choose a combination, which will release the therapeutic agent over a desired time period ranging between about one day and about six months.

In yet other embodiments, further excipients are employed. The amount of excipient that is useful in the composition of this invention is an amount that serves to uniformly distribute the therapeutic agent throughout the composition so that it can be uniformly dispersed when it is to be delivered to a subject in need thereof. It may serve to dilute the therapeutic agent to a concentration at which the therapeutic agent can provide the desired beneficial palliative or curative results while at the same time minimizing any adverse side effects that might occur from too high a concentration. It may also have a preservative effect. Thus, for the therapeutic agent that has high physiological activity, more of the excipient will be employed. On the other hand, for the therapeutic agent compound that exhibits a lower physiological activity a lesser quantity of the excipient will be employed. In general, the amount of excipient in the composition will be between about 50% weight (w) and 99.9% w. of the total composition. For the therapeutic agent that has a particularly high physiological activity, the amount will be between about 98.0% and about 99.9% w.

Accordingly, the methods of creating the sustained-release formulations comprising the at least one anti-inflammatory compound, at least one lubricating agent, and/or the additive are within the expertise of the person having ordinary skill in the art. The combination of all three listed compounds is also disclosed.

Suitable examples of lubricants include, without limitations, hyaluronic acid, hyaluronan, lubricin, polyethylene glycol, and any combinations thereof.

The therapeutic agent may be administered locally. In one embodiment, therapeutic agent has a targeted release rate, and is injected into the facet joint. In another embodiment, a controlled administration system releases the therapeutic agent. The controlled administration system may be, for example, a depot, an infusion pump, an osmotic pump, or an interbody pump. The controlled administration system may be implanted adjacent to the facet joint, or protruding into the facet joint.

In another embodiment the therapeutic agent is administered outside of the facet joint space and allowed to migrate inside. An advantage of this embodiment is that it is not necessary to pierce the facet joint capsule to deliver the therapeutic agent. Suitable delivery can be made through a patch and/or a gel to the exterior of the facet joint capsule and/or to the subchondral bone.

In another embodiment the therapeutic agent may be injected into subchrondral bone. In another embodiment the therapeutic agent may be injected near the facet joint.

In yet another embodiment, the controlled administration system may be at least partially implanted within the facet joint. In a specific embodiment, the controlled administration system comprises a catheter adjacent to the facet joint, the catheter having a proximal end and a distal end, the distal end having an opening to deliver in situ, the proximal end being fluidly connected to a pharmaceutical delivery pump.

A "depot" includes but is not limited to capsules, microspheres, particles, gels, coatings, matrices, wafers, pills or other pharmaceutical delivery compositions for containing one or more active ingredients. A depot may comprise a biopolymer. The biopolymer may provide for non-immediate release of the one or more active ingredients. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, or combinations thereof.

"Localized" delivery is defined herein as non-systemic delivery in which a therapeutic agent is deposited within the facet joint or in close proximity within about 5 cm, or preferably within about 1 cm.

A "controlled administration system" provides localized delivery of one or more active ingredients in a quantity of that can be deposited at the target site as needed for pain, either continuously or at an intermittent rate. A "controlled administration system" includes, but is not limited to, a bolus of the therapeutic agent, a depot, an osmotic pump, an interbody pump, an infusion pump, implantable mini-pumps, a peristaltic pump, other pharmaceutical pumps, or a system administered locally by insertion of a catheter into, at or near a disc, the catheter being operably connected to a pharmaceutical delivery pump. It is understood that pumps can be internal or external as appropriate.

This embodiment is especially preferable. This should allow administration of the therapeutic agent at a lower effective dose versus systemic or oral administration. In another embodiment the therapeutic agent may be injected into subchrondral bone.

A person skilled in the art will appreciate that various modifications of this embodiment are possible. Among these modifications are different sustained-release formulations of the therapeutic agent and additive.

Hydrogels

Hydrogels can also be used as a sustained release device to deliver the therapeutic in a time-release manner to the joint environment. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the therapeutic agent at the application site, thereby eliminating undesired migration from the facet joint. The hydrogels are also biocompatible, e.g., not toxic, to any cells suspended in the hydrogel.

In an embodiment the hydrogel is a therapeutic agent and can be administered into a facet joint. The therapeutic effect of the hydrogel can include, but is not limited to, hydration or lubrication of the facet joint space.

Hydrogels suitable for use in the present invention include water-containing gels, i.e., polymers characterized by hydrophilicity and insolubility in water. See, for instance, "*Hydrogels*", pages 458-459 in *Concise Encyclopedia of Polymer Science and Engineering*, Eds. Mark et al., Wiley and Sons (1990), the disclosure of which is incorporated herein by reference. By virtue of their hydrophilic, water-containing nature, hydrogels can house viable cells, such as mesenchymal stems cells, and assist with load bearing capabilities of the facet joint.

In an embodiment, the hydrogel is a fine, powdery synthetic hydrogel. Suitable hydrogels exhibit an optimal combination of such properties as compatibility with the matrix polymer of choice, and biocompatibility. The hydrogel can include any of the following: polysaccharides, proteins, polyphosphazenes, poly(oxyethylene)-poly(oxypr-opylene) block polymers, poly(oxyethylene)-poly(oxypropylene) block polymers of ethylene diamine, poly(acrylic acids), poly (methacrylic acids), copolymers of acrylic acid and methacrylic acid, poly(vinyl acetate), and sulfonated polymers. The hydrogel can be administered in a dehydrated state and be allowed to hydrate within the facet joint space, creating a temporary or lasting spacer within the facet joint. Alternatively or in addition, this method of administration can increase the hydration within the facet joint space.

Anti Inflammatory Agents

The present invention can further comprise non-steroidal anti-inflammatory agents (NSAIA) including glutamate antagonists, TNF-alpha inhibitors. In some embodiments, the non-steroidal anti-inflammatory agents is anabolic, and is selected from the group consisting of TOLMETIN™ (available from Ortho-McNeil), SUPROL™ (available from Johnson & Johnson), and Tiaprofenic acid, (available from Roussel Labs). In some embodiments, the NSAIA is a dual inhibitor of both the COX and LOX pathways, for example TEPOXALIN™ (available from Johnson & Johnson).

In addition, anti-cathepsins may also be used in accordance with the present invention. It is believed that inhibition of these enzymes inhibits the breakdown of the extracellular matrix. Suitable antagonists inhibit a cathepsin selected from the group consisting of cathepsin B, cathepsin L and cathepsin K.

In addition, cycline compounds may also be used in accordance with the present invention. Suitably, the cycline compound is administered in an amount effective to inhibit the action of a pro-inflammatory cytokine (such as TNF-α) or MMP. Suitably, the cycline compound is administered in an amount effective to inhibit the action of an MMP released by cells during the degenerative process.

In some embodiments, the cycline compound is selected from the group of cycline compounds consisting of doxycycline, lymecycline, oxicycline compound, tetracycline, minocycline, chemically modified cycline compound (CMT) and KB-R7785. Preferably, doxycycline is selected.

Diagnostic Methods

Because the causes of joint pain may be myriad, and because of the significant cost involved it would be useful for the clinician to first perform a diagnostic comprising Magnetic Resonance Imaging, assays using enzyme-linked immunoabsorbent assay (as per Burke, Br. JBJS, 84-B(2) (2002). In some embodiments, the invasive test may be performed during arthroscopy.

In some embodiments, the diagnostic methods can include diagnostic tools for detecting TNF-α, IL-1β, or other inflammatory cytokines.

In some embodiments, a bioMEMS device containing a "lab on a chip" can be used in the diagnostic test.

In another embodiment, the diagnostic test comprises evaluating the genetic makeup of the patient and forecasting whether that patient will have a degenerative facet joint in the future.

A person of ordinary skill in the art will recognize that the threshold for pain may vary between different patients. Accordingly, the results of the diagnosing pain, the testing of the potential candidates to relieve pain, and/or the monitoring of pain may be correlated with the pain measurements according to techniques of pain assessment known in the art. Such correlation enable the practitioner to choose the course of treatment which better fits the needs of the patient. The techniques of pain assessment include, without limitation, VAS, Oswestri, and SF-36 Questionnaires.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

We claim:

1. A method for treating a facet pain in a subject comprising providing an effective amount of therapeutic agent whereby a biological repair effect on the facet joint is produced as compared to a temporary anti-inflammatory effect, wherein the effective amount of the therapeutic agent is uniformly dispersed in a depot with an effective amount of a non-steroid anti-inflammatory agent, BMP-2 and a lubricating agent comprising lubricin, wherein the depot comprises a dehydrated hydrogel containing a biodegradable polymer comprising copolymers of L-glutamic acid and gamma ethyl-L-glutamate that releases the therapeutic agent over a period of one day to six months.

2. The method of claim 1 wherein the effective amount of the therapeutic agent is administered to treat defects selected from the group consisting of articular cartilage surface defects, small ligamentous facet joint capsule tears, and subchondral bone defects, and combinations thereof.

3. The method of claim 1 wherein the facet joint is in an early stage of degeneration.

4. The method of claim 1 wherein the therapeutic agent is a soft tissue cytokine.

5. The method of claim 1 wherein the therapeutic agent further comprises GDF, CDMP, TGF, PDGF, IGF, FGF, Statin, LMP, soft tissue cytokines, cells, hyaluronic acid, chondroitin sulfate based polymers, polyethylene glycol, PPF, polyvinylalcohol, and collagen, and mixtures thereof.

6. The method of claim 1 wherein the therapeutic agent further comprises LMP, soft tissue cytokines, cells, hyaluronic acid, and mixtures thereof.

7. The method of claim 1 wherein the therapeutic agent is LMP.

8. The method of claim 1, wherein the effective amount of the therapeutic agent is administered through the depot, which is implanted into the facet joint or protruding into the facet joint.

9. The method of claim 1 wherein the depot is implanted into the subchrondral bone.

10. The method of claim 1 wherein the depot is administered to the exterior of the facet joint capsule and/or subchondral bone.

11. A method for repairing the articular cartilage surface of a facet joint comprising providing an effective amount of therapeutic agent comprising LMP and BMP-2 uniformly dispersed in a depot with an effective amount of a non-steroidal anti-inflammatory agent and a lubricating agent comprising lubricin, wherein the depot comprises a dehydrated hydrogel containing a biodegradable polymer comprising copolymers of L-glutamic acid and gamma ethyl-L-glutamate that releases the therapeutic agent over a period of one day to six months, whereby a biological repair effect on the facet joint is produced as compared to a temporary anti-inflammatory and lubricating agent effect.

12. A method for treating a facet pain in a subject comprising:
providing an effective amount of therapeutic agent comprising LMP BMP-2, a dehydrated hydrogel, an anti-inflammatory agent, and a lubricant uniformly dispersed in a depot comprising copolymers of L-glutamic acid and gamma ethyl-L-glutamate that releases the therapeutic agent over a period of one day to six months, wherein the lubricant comprises lubricin; and creating a lasting or a temporary spacer within the facet joint; whereby a biological repair effect on the facet joint is produced as compared to a temporary anti-inflammatory effect, wherein the facet joint is in an early stage of degeneration.

* * * * *

UNITED STATES PATENT AND TRADEMARK OFFICE
CERTIFICATE OF CORRECTION

PATENT NO.         : 8,057,458 B2
APPLICATION NO.    : 11/589410
DATED              : November 15, 2011
INVENTOR(S)        : McKay et al.

Page 1 of 1

It is certified that error appears in the above-identified patent and that said Letters Patent is hereby corrected as shown below:

On the Title Page, in Item (56), under "OTHER PUBLICATIONS", in Column 2, Line 6, delete "polyetheylene" and insert -- polyethylene --, therefor.

On the Title Page, in Item (56), under "OTHER PUBLICATIONS", in Column 2, Line 9, delete "cinically" and insert -- clinically --, therefor.

IN THE SPECIFICATIONS:

In Column 5, Line 2, delete "osteoprogentior" and insert -- osteoprogenitor --, therefor.

In Column 5, Line 27, delete "compressability," and insert -- compressibility, --, therefor.

In Column 7, Line 45, delete "subchrondral" and insert -- subchondral --, therefor.

In Column 8, Lines 23-24, delete "subchrondral" and insert -- subchondral --, therefor.

IN THE CLAIMS:

In Column 10, Line 46, in Claim 9, delete "subchrondral" and insert -- subchondral --, therefor.

In Column 10, Line 65, in Claim 12, delete "LMP" and insert -- LMP, --, therefor.

Signed and Sealed this
Third Day of January, 2012

David J. Kappos
*Director of the United States Patent and Trademark Office*